United States Patent
Lell et al.

(10) Patent No.: US 10,792,429 B2
(45) Date of Patent: Oct. 6, 2020

(54) NEEDLELESS INJECTION DEVICE WITH DOUBLE MEMBRANE

(71) Applicant: Peter Lell, Moosburg (DE)

(72) Inventors: Peter Lell, Moosburg (DE); Cihad Anamur, Ludwigshafen (DE); Christian Fellner, Ilmmünster (DE); Gerhard Winter, Penzberg (DE); Julia Engert, Munich (DE)

(73) Assignee: Peter Lell (DE)

( * ) Notice: Subject to any disclaimer, the term of this patent is extended or adjusted under 35 U.S.C. 154(b) by 0 days.

(21) Appl. No.: 15/320,805

(22) PCT Filed: Jun. 24, 2015

(86) PCT No.: PCT/EP2015/064304
§ 371 (c)(1),
(2) Date: Dec. 21, 2016

(87) PCT Pub. No.: WO2015/197724
PCT Pub. Date: Dec. 30, 2015

(65) Prior Publication Data
US 2017/0197034 A1    Jul. 13, 2017

(30) Foreign Application Priority Data
Jun. 24, 2014    (EP) .................................. 14173786

(51) Int. Cl.
*A61M 5/30*    (2006.01)

(52) U.S. Cl.
CPC ............ *A61M 5/30* (2013.01); *A61M 5/3015* (2013.01); *A61M 2205/8206* (2013.01)

(58) Field of Classification Search
CPC .... A61M 5/2046; A61M 5/2053; A61M 5/30; A61M 5/3015
See application file for complete search history.

(56) References Cited

U.S. PATENT DOCUMENTS

| 3,308,818 A | 3/1967 | Rutkowski |
| 5,399,163 A | 3/1995 | Peterson et al. |
| (Continued) | | |

FOREIGN PATENT DOCUMENTS

| DE | 102007004211 A1 | 7/2008 |
| EP | 1557190 A1 | 7/2005 |
| (Continued) | | |

OTHER PUBLICATIONS

International Search Report for PCT/EP2015/064304 dated Oct. 2, 2015.
(Continued)

*Primary Examiner* — Emily L Schmidt
(74) *Attorney, Agent, or Firm* — Faegre Drinker Biddle & Reath LLP

(57) ABSTRACT

The invention relates to a needleless injection device or a device for the needleless injection of a substance into a tissue or body, with which device a substance, in particular an active substance, can be injected by means of high pressure. A device according to the invention comprises a chamber (11) containing a pyrotechnic material, wherein the chamber has a fixed double membrane (13, 15) at a discharge opening, wherein the skin-side membrane (15) of the double membrane (13, 15) is provided with a substance application (25).
A successful injection lies in the fact that sufficient substance is introduced into the body through the tissue barrier or body barrier, in particular such as the skin.

14 Claims, 2 Drawing Sheets

(56) References Cited

U.S. PATENT DOCUMENTS

| | | | |
|---|---|---|---|
| 6,010,478 A | 1/2000 | Bellhouse et al. | |
| 6,258,063 B1* | 7/2001 | Haar | A61M 5/2425 222/633 |
| 6,604,612 B2 | 8/2003 | Nagy et al. | |
| 6,837,866 B1* | 1/2005 | Alexandre | A61M 5/3015 604/69 |
| 6,913,593 B1 | 7/2005 | Alexandre et al. | |
| 7,160,265 B2 | 1/2007 | Lell | |
| 8,262,604 B2 | 9/2012 | Asmussen et al. | |
| 2002/0004641 A1* | 1/2002 | Bellhouse | A61M 5/3015 604/68 |
| 2002/0091353 A1* | 7/2002 | Bellhouse | A61M 5/3015 604/68 |
| 2002/0153209 A1 | 10/2002 | Nagy et al. | |
| 2002/0188248 A1* | 12/2002 | Bellhouse | A61M 5/3015 604/68 |
| 2004/0162517 A1* | 8/2004 | Furst | A61M 5/2046 604/69 |
| 2007/0038175 A1 | 2/2007 | Van Laar | |
| 2010/0179473 A1* | 7/2010 | Genosar | A61M 5/14248 604/70 |

FOREIGN PATENT DOCUMENTS

| | | |
|---|---|---|
| JP | S51127081 U | 10/1976 |
| JP | 2001511037 A | 8/2001 |
| JP | 2003530531 A | 10/2003 |
| JP | 2008128278 A | 6/2008 |
| WO | WO-9831409 A2 | 7/1998 |
| WO | WO-0141839 A1 | 6/2001 |
| WO | WO-2004071558 A1 | 8/2004 |

OTHER PUBLICATIONS

Written Opinion of the International Searching Authority for PCT/EP2015/064304 dated Oct. 2, 2015.

\* cited by examiner

NEEDLELESS INJECTION DEVICE WITH DOUBLE MEMBRANE

CROSS-REFERENCE TO RELATED APPLICATIONS

This application is a national stage application (under 35 U.S.C. § 371) of PCT/EP2015/064304, filed Jun. 24, 2015, which claims benefit of European Application No. 14173786.6, filed Jun. 24, 2014, both of which are incorporated herein by reference in their entirety.

The invention relates to a needleless injection device or a device for needleless injection of a substance into a tissue or body, with which device a substance, in particular an active substance, can preferably be injected by means of high pressure. A successful injection lies in the fact that sufficient substance is introduced into the body through the tissue barrier or body barrier, in particular such as the skin. The basic principle of injecting a substance in a needleless manner by means of high pressure has been known for some time (for example see U.S. Pat. No. 3,308,818).

Various types of needleless injection devices are described in the prior art, for example (not exhaustively) a cylinder-piston unit comprising a pretensioned spring element (DE 10 2007 004 211 A1) or by means of what are known as injection cartridges (WO 98/31409) and by means of a gas cartridge for acting on a piston (U.S. Pat. No. 5,399,163).

Furthermore, needleless injection devices can consist of a pyrotechnic drive, which for example is used to actuate a piston and in this way causes an active substance to be pressed out from a cannula (EP 1 557 190 A1).

A further embodiment of a needleless injection device lies in a pyrotechnic approach, in which case an explosion is generated in a chamber (also referred to as a firing chamber), wherein the released energy is used to transfer a pulse to a membrane, whereby a substance adsorbed by the membrane is sufficiently accelerated and detaches from the membrane in the direction of the tissue.

A generic device of this type is disclosed in WO 2004/071558 A1. However, a generic embodiment of this type can still be improved. In particular, it is disadvantageous in accordance with the teaching of WO 2004/071558 that the provided membrane can rupture, and consequently there is no guarantee that parts of the membrane and also the exhaust gases from the firing chamber/combustion chamber will not reach the tissue and damage the tissue or body.

The present invention therefore makes reference to a generic embodiment according to WO 2004/071558, but addresses the objective problem of keeping membrane parts and exhaust gases away from the tissue or a body.

The invention therefore relates to a needleless injection device comprising a (firing) chamber (11) containing a pyrotechnic material, wherein the chamber (11) has a fixed double membrane (13, 15) at a discharge opening, wherein the skin-side membrane (15) of the double membrane is provided with a substance application (25).

The membrane (13) on the firing chamber side leads into the firing chamber (11) and combustion chamber (24) thereof.

A fundamental and generic design is shown in FIG. 1 together with a key, wherein, for the function of the injection device according to the invention, the housing (22) and also the parts (7) to (16) should be taken into consideration. Here, the parts (7) to (16) can be installed readily in a differently formed housing (22), and a detonator, in particular an EED (10), can also be supplied differently with energy, without modifying the function of the parts or the device. Specific embodiments will be described in greater detail.

The geometry of the individual parts in FIG. 1 can be modified or integrally combined in part depending on the requirements. By way of example, parts (7) to (9) can be integrally combined to form one part, or the part (7) can be omitted, for example if part (8) has an external thread and is screwed into the housing (22) (or for example is held in the housing (22) by retaining ring) or is an insertion part in the injection mould of the housing (22) (see also FIG. 2). The parts (1) and also the parts (4) to (6) and (23) can also be omitted by the use of a conventional button to place the detonator (EED) (10) in electrical contact with the battery (3).

Within the scope of this invention, a "pyrotechnic material" is understood to mean any material which can be made to explode using activation energy. These materials for example can be solid or gaseous substances, such as azides, tetrazene, etc. or other pyrotechnic materials known to a person skilled in the art. In accordance with the invention the explosion energy should allow a sufficient pulse transfer to the fixed double membrane (13, 15) according to the invention, such that the applied substance (25) can be detached, accelerated, and brought to high speeds.

The pyrotechnic material is contained in a chamber (11) in accordance with the invention, more specifically in the combustion chamber (24), wherein the necessary activation energy for generating explosion energy is provided preferably by means of a detonator (10), in particular by means of a mini detonator (EED) (10).

The necessary activation energy for triggering an explosion in the chamber (11) can therefore be provided by means of an activation unit, in particular (not exhaustively) a detonator (10), igniter, firing pin, or ignition piece, more specifically via a triggering mechanism by means of friction, impact or suitable power supply. A suitable activation unit is illustrated in FIG. 1 by way of example. The battery (3) is pressed against a contact spring (6) and against a contact pin (5) by means of a trigger or button (1) in that the electrical circuit is closed via the connections (9) and the EED (10), consequently igniting the EED (10). Alternative triggering mechanisms are known to a person skilled in the art (friction wire, jumper wire, clicker mechanism beating against impact-sensitive ignition mixture, etc.).

In a further preferred embodiment said activation unit (1, 2, 3, 4, 5, 6, 7, 8, 9, 10) is oriented in the axial direction relative to the chamber (11) inclusive of combustion chamber (24) and opposite the fixed double membrane (13, 15).

By way of example, with sugar particles 20 to 80 μm in size as applied substance (25), speeds of approximately 600 m/sec or more can be achieved in accordance with the invention. Larger particles penetrate much more easily into the tissue or the body on account of their pulse and the growing ratio of density to radius, whereas smaller particles by contrast require a much higher speed than the specified 600 m/sec.

If slower speeds of the particles accelerated through the double membrane up to approximately 400 m/sec are sufficient, a conventional igniter with or without additional charge can also be used instead of the detonator 10.

Within the scope of this invention the term "pulse transfer" is also understood synonymously to mean a transfer or application of force or pressure which in any case is sufficient to detach the substance(s) (25) applied to the skin-side membrane (15) of the double membrane (13, 15) and to accelerate this/these to the desired high speeds, whereby they initially fly freely in the direction of the tissue or skin

(18) or body in order to strike there, break through the tissue or body barrier, and penetrate to the desired depth of the tissue, in particular skin or body.

Within the scope of this invention, "skin" means a tissue barrier of a human being, mammal, or animal. The skin, as the largest organ of the human body, performs numerous vital functions, and in particular the epidermis serves as a barrier organ. This barrier function is maintained inter alia by skin lipids. These epidermal lipids, such as glycosphingoloids, ceramides, sterols and sterol esters, fatty acids, tryglycerides, n-alkanes or various polar lipids, are released in the keratinisation process. By means of the needleless or needle-free application according to the invention, the substances consequently can enter the body locally and can lead into the bloodstream as appropriate.

In a further embodiment the combustion chamber (24) in the chamber (11) can be provided preferably with a viscous, thick mass, such as fat, oils and the like, for the purpose of reducing the size of the empty space in the combustion chamber (24) and thus increasing the pressure rise in the event of a small charge of the detonator (EED) (10).

The chamber (11) preferably has O-rings for sealing (12). Furthermore, the chamber (11) can have a vent (20) inclusive of associated cover (21).

As already mentioned above, the generic document WO 2004/071558 indeed discloses a membrane, but no fixed double membrane (13, 15) according to the invention. In particular, the following embodiments allow an effective pulse transfer to the fixed double membrane in the sense of this invention.

In a preferred embodiment the fixed double membrane (13, 15) according to the invention, i.e. preferably both the skin-side membrane (15) and the membrane (13) on the firing chamber side, consists of metal or a material of corresponding hardness and ductility, such as steel, plastics, but particularly preferably titanium or sheet titanium. In particular, titanium has an advantageous high formability limit alongside good capacity to be accelerated due to its lower specific density compared to steel and plastics, whereby with relatively low pressures in the firing chamber a much quicker speed of the buckling membrane is achieved. Here, the acceleration index AI=sigma 0.2/ro is key. The membranes (13, 15) are also level or closed, i.e. are without holes, recesses, etc.

Compared to a single membrane, the fixed double membrane here provides a greater operational safety in the case of material faults or overload (if a membrane tears, exhaust gas still does not pass outwardly) with a much better deformability, which makes it possible to minimise the energy losses when the double membrane is deformed (i.e. for example instead of a single membrane 1 mm thick, two membranes each 0.5 mm thick are placed one on top of the other so as to form a double membrane. Other thickness ratios are also possible, such as 0.6 mm in the direction of the firing chamber and 0.4 mm in the direction of the skin).

The term "fixed double membrane" (13, 15) means that both membranes (the double membrane) are attached/fixed with a support disc (16), in particular to the chamber (11) and consequently are immovable, i.e. are locked, and the fixed double membrane or the membrane (13) on the firing chamber side leads directly into the chamber (11) or the combustion chamber (24) (see FIG. 1). It is also preferred that the inwardly directed membrane (13) on the firing chamber side has a thickness of from 0.1 mm to 0.6 mm, preferably 0.2 mm to 0.6 mm, particularly preferably 0.5 mm. The outwardly directed skin-side membrane (15) preferably likewise has a thickness of from 0.1 mm to 0.6 mm, preferably 0.2 mm to 0.6 mm, particularly preferably 0.5 mm. The membranes (13, 15) can contact one another wholly or partially.

In a further preferred embodiment, however, the membrane (13) on the firing chamber side has a distance from the skin-side membrane (15), more specifically preferably of from 0.2 mm to 1.5 mm, particularly preferably 1 mm. The necessary spacing can be provided by means of a spacer (14) between the two membranes. This measure causes an efficient prevention of the rupturing or bursting of the skin-side membrane.

As illustrated in FIG. 1 the outer surfaces of membranes 13, 15 are sandwiched between disc 16 and an outer wall of chamber 11. As shown in FIG. 2 spacer 14 separates membranes 13 and 15 from each other to create an open area between the membranes 13, 15 in line with the combustion chamber 24.

In a further particularly preferred embodiment, the double membrane (13, 15) is completely or partially curved towards the chamber (11) and into the combustion chamber (24) thereof, over the entire area or preferably in the central radial region about a circle midpoint. Such a concave curvature of the membranes from the viewpoint of the firing chamber can be achieved by a person skilled in the art by means of known methods. Said curvature of the double membranes (13, 15) according to the invention additionally allows an advantageous increased speed of from 10 to 15%, together with focussing and acceleration of the applied substances (25) in the direction of the skin (18)—presumably by shock wave focussing.

In a further preferred embodiment, the two membranes (13, 15) have support discs (16). The support discs are preferably made of plastic, brass, etc., which is particularly suitable for energy absorption. In addition, the support disc is adapted in terms of energy, preferably with a tapering towards to the skin (18). At the same time, the support disc (16) can be thinly coated on its inner contour with a soft plastic, for example with polyethylene, so as to advantageously significantly reduce the triggering noise of the device—for example the snap like noise created when a metal membrane impacts on a metal support disc is avoided.

The support disc additionally also has the task of reducing the energy of the membranes once pressure has been applied thereto and of lastingly intercepting the pressure still acting in the firing chamber after triggering, and of supporting the membranes.

The aforementioned embodiments advantageously allow reliable prevention or rupture or bursting of at least the outer (skin-side) membrane of the double membrane. Furthermore, the applied substances advantageously experience an optimised pulse transfer or acceleration at very high speeds up to 800 m/sec.

As illustrated the support disc (16) is separate and distinct from the remainder of the device. The support disc (16) is confined in the housing (22) by a part (27) longitudinally outwardly of and longitudinally in line with the support disc (16). The support disc (16) has a central opening (26) in line with a central opening (28) of the part (27) for passage of substrate application (25) from the skin-side membrane (15). As illustrated in FIG. 2 the spacer (14) is a layer having a flat surface on one side for complete surface to surface contact with the firing side membrane (13) and an opposite side flat surface for complete surface to surface contact with the skin-side membrane (15). The spacer (14) has an open area centrally located in the spacer (14).

Within the scope of this invention, "applied substances (25)" means substances that contain a material and for example are fixed with oils inter alia to the outer (skin-side) membrane or stick by means of adhesion, wherein the applied substances (25) are applied to the skin side of the skin-side membrane (15). By way of example, the applied substances can contain agents which allow the active substance to dry on said membrane. In particular, additional adhesion promoters or additives are suitable and are added, such as oils or other preferably pharmaceutically suitable auxiliaries and additives.

The term "substances" includes all agents and materials which are suitable for the appropriate application to the membrane (for example powder, particles, etc.), including one or more active substances (for example medicinal drugs).

In a further embodiment the injection device can contain an attachment (17), which is ergonomically adapted to the tissue or skin (18) against which said device is placed.

Bores or milled portions can also be formed in the attachment (17), which allow air also accelerated at the same time as the acceleration of the double membrane to flow off parallel to the surface and which prevent a hydraulic coupling of the skin to the central bore via the double membrane, which would inadmissibly load the contacted skin with gas pressure.

The invention also relates to the use or application of one or more substances, in particular active substances, in particular a medicinal drug for needle-free application by means of the injection device according to the invention in accordance with one of the above embodiments.

The invention also relates to the use or application of substances, in particular substances having any function and suitability, such as dyes or lubricants or materials having other particular properties for needleless insertion into surfaces or the body of technical subjects by means of the injection device according to the invention in accordance with one of the above embodiments.

The invention therefore relates to an injection device according to any one of the above embodiments for use of a substance or an active substance, in particular a medicinal drug, for needle-free application.

The following examples and Figures are intended to explain the invention in greater detail, without limiting it.

KEY

Figure 1:
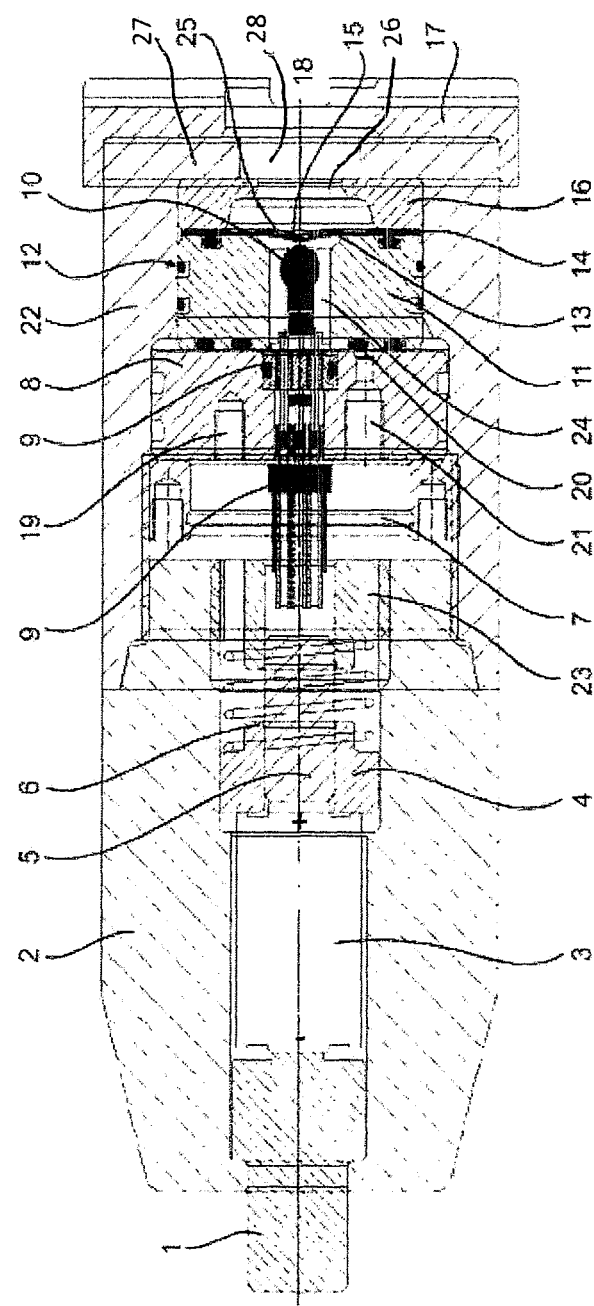
FIG. 1 shows a cross-section of the injection device according to the invention.
Figure 2:
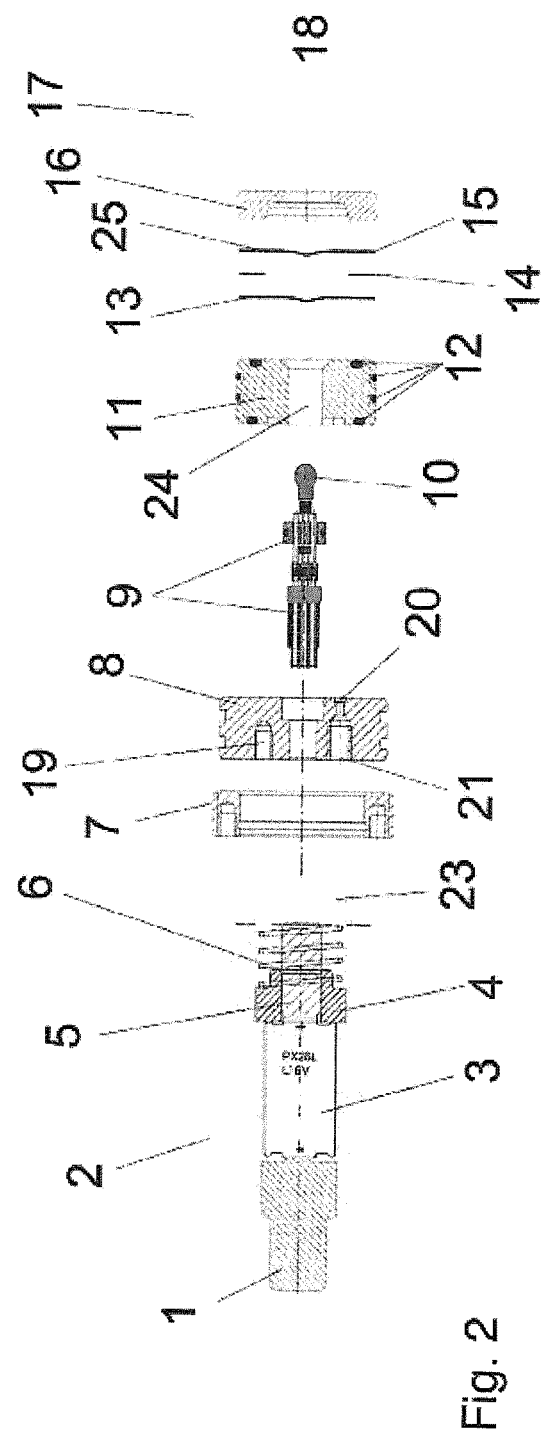
FIG. 2 shows more clearly the parts for producing the injection device according to the invention.

1 trigger, button
2 trigger housing
3 battery
4 spring cap
5 contact pin
6 contact spring
7 grooved nut
8 holder for glass feedthrough
9 glass feedthrough with connections
10 mini detonator or ignition piece, EED
11 firing chamber or chamber
12 O-ring seal of the firing chamber (can also be omitted in some embodiments of the device)
13 membrane on the firing chamber side, fixed to the chamber (11)
14 pacer, also performs sealing functions
15 skin-side membrane, fixed to membrane (13) and spacer (14)
16 support disc
17 attachment
18 skin or the surface to be penetrated (bears against 17, not shown)
19 thread for ground connection thread (can also be omitted in some embodiments of the device)
20 firing chamber vent
21 cover, vent
22 housing for parts 7-21
23 guide for contact pin
24 combustion chamber
25 substance application
26 support disc opening
27 part
28 opening of part (27)

The invention claimed is:

1. A needleless injection device comprising a housing (22) having a firing chamber (11) containing a pyrotechnic material, a combustion chamber (24) in the firing chamber (11), the firing chamber having a discharge opening, a fixed double membrane (13, 15) comprising a firing side membrane (13) and a skin-side membrane (15) at the discharge opening, the double membrane (13, 15) being attached/fixed by the firing side membrane (13) and the skin-side membrane (15) being sandwiched between a wall of the firing chamber and at least one support disc (16) within the housing (22), and the skin-side membrane (15) being provided with a substance application (25), the substance application (25) being applied to a side of the skin-side membrane (15) remote from the firing side membrane (13) whereby the substance application (25) is detached from the skin-side membrane (15) by the application of force or pressure to move toward and contact a user, the support disc (16) being separate and distinct from the remainder of the device, the support disc (16) being confined in the housing (22) by a part (27) longitudinally outwardly of and longitudinally in line with the support disc (16), the support disc (16) having a central opening (26) in line with a central opening (28) of the part (27) for passage of the substance application (25) from the skin-side membrane (15), and the support disc (16) being made from an energy absorption material, and the firing side membrane (13) and the skin-side membrane (15) are in complete surface to surface contact with each other.

2. The needleless injection device according to claim 1, wherein the membrane (13) on the firing chamber side has a thickness of from 0.1 mm to 0.6 mm, and the skin-side membrane (15) has a thickness of from 0.1 mm to 0.6 mm.

3. The needleless injection device according to claim 1, wherein the fixed double membrane (13, 15) consists of metal, steel, titanium or sheet titanium.

4. The needleless injection device according to claim 1, wherein the membrane on the firing chamber side, and also the skin-side membrane are curved towards the chamber (11), at least partially.

5. The needleless injection device according to claim 1, wherein an activation unit (1, 2, 3, 4, 5, 6, 7, 8, 9, 10) is oriented in the axial direction relative to the chamber (11) and is opposite the fixed double membrane (13, 15).

6. The needleless injection device according to claim 1, containing an attachment (17) with bores or milled portions formed therein.

7. The needleless injection device according to claim 1 wherein the central opening of the support disc (16) tapers away from the skin-side membrane (15).

8. The needleless injection device according to claim 1 including an attachment (17) outwardly of the support disc (16) and the part (27) to be placed against a patient, and the attachment (17) having a central opening in line with the central opening of the support disc (16) and the central opening of the part (27).

9. A needleless injection device comprising a housing (22) having a firing chamber (11) containing a pyrotechnic material, a combustion chamber (24) in the firing chamber (11), the firing chamber having a discharge opening, a fixed double membrane (13, 15) comprising a firing side membrane (13) and a skin-side membrane (15) at the discharge opening, the skin-side membrane (15) being provided with a substance application (25), the substance application (25) being applied to a side of the skin-side membrane (15) remove from the firing side membrane (13) whereby the substance application (25) is detached from the skin-side membrane (15) by the application of force or pressure to move toward and contact a user, a spacer (14) being between and in contact with the firing side membrane (13) and the skin-side membrane (15) creating an open area between the firing side membrane (13) and the skin-side membrane (15) in line with the combustion chamber (24), the spacer functioning to prevent rupturing or bursting of the skin-side membrane, the spacer (14) being a layer having a flat surface on one side in complete surface to surface contact with the firing side membrane (13) and an opposite side flat surface in complete surface to surface contact with the skin-side membrane (15), and the spacer (14) having an open area centrally located in the spacer (14) to prevent rupturing or bursting of the skin-side membrane (15).

10. The needleless injection device according to claim 9, wherein the spacer (14) also has a sealing function.

11. The needleless injection device according to claim 9, wherein the firing side membrane (13) and the skin-side membrane (15) are spaced apart by a distance of from 0.2 mm to 1.5 mm.

12. The needleless injection device according to claim 9, wherein each of the firing side membrane (13) and the skin-side membrane (15) has a thickness of from 0.1 mm to 0.6 mm.

13. The needleless injection device according to claim 9, wherein at least one support disc (16) and the chamber (11) are in a housing (22), and the firing side membrane (13) and the skin-side membrane (15) being sandwiched between a wall of the chamber (11) and the at least one support disc (16).

14. The needleless injection device according to claim 9, wherein the double membrane (13, 15) consists of titanium or sheet titanium.

* * * * *